US00PP17064P2

(12) United States Plant Patent
Olesen et al.

(10) Patent No.: US PP17,064 P2
(45) Date of Patent: Aug. 29, 2006

(54) FLORIBUNDA ROSE PLANT 'POULDOM'

(50) Latin Name: *Rosa hybrida*
Varietal Denomination: POULdom

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 372 days.

(21) Appl. No.: 10/647,012

(22) Filed: Aug. 21, 2003

(51) Int. Cl.
*A01H 5/00* (2006.01)

(52) U.S. Cl. ..... Plt./145

(58) Field of Classification Search ..... Plt./145
See application file for complete search history.

(56) References Cited

PUBLICATIONS

UPOVROM Plant Variety Database 2005/05 cited for 'Pouldom' cultivar.*

* cited by examiner

*Primary Examiner*—Kent Bell
*Assistant Examiner*—Annette H Para

(57) ABSTRACT

A new floribunda garden rose plant which has abundant, golden-yellow flowers and attractive foliage. This new and distinct variety has shown to be uniform and stable in the resulting generations from asexual propagation.

1 Drawing Sheet

Classification: Botanical: *Rosa hybrida* 'POULdom'. Commercial: Floribunda.

SUMMARY OF THE INVENTION

The present invention constitutes a new and distinct variety of garden rose plant which originated from a controlled crossing between 'KORfalt' and an unnamed seedling, both unpatented varieties. The two parents were crossed during the summer of 1987 and the resulting seeds were planted in a controlled environment in Fredensborg, Denmark. The new variety is named 'POULdom'.

The new rose may be distinguished from its seed parent, 'KORfalt', by the following combination of characteristics:

1. The seed parent is a yellow floribunda with red intonations on its outer petals, while 'POULdom' is a golden yellow floribunda.
2. The seed parent has a typical petal count of 35, while that of 'POULdom' is 20 to 25.

The new variety may be distinguished from its pollen parent, an unnamed seedling, by the following combination of characteristics:

1. The pollen parent is a clear yellow flower and 'POULdom' is a golden-yellow flower.
2. 'POULdom' is a semi-double rose exhibiting 20–25 petals while the pollen parent is a double rose averaging 35 petals.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULdom' from all other varieties of which we are aware.

As part of their rose development program, L. Pernille Olesen and Mogens N. Olesen germinated the seeds from the aforementioned hybridization during winter 1987 and conducted evaluations on the resulting seedlings in a controlled environment in Fredensborg, Denmark.

'POULdom' was selected in the spring 1998 by the inventors as a single plant from the progeny of the aforementioned hybridization.

Asexual reproduction of 'POULdom' by traditional budding and rooted cuttings was first done by L. Pernille and Mogens N. Olesen in their nursery in Fredensborg, Denmark in August, 1998. This initial and other subsequent asexual propagations conducted in controlled environments have demonstrated that the characteristics of 'POULdom' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULdom'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULdom', as observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULreb', a rose variety from the same inventors described and illustrated in U.S. Plant patent application Ser. No. 09/287,295 dated Mar. 31, 1999 are compared to 'POULdom' in Chart 1.

CHART 1

| | 'POULdom' | 'POULreb' |
|---|---|---|
| Bud color, as sepals first divide | Yellow-Orange Group 17B–D | Yellow Group 4C |
| Color, upper surface, upon opening | Yellow Group 9A–9C | Yellow Group 7B at base and Yellow Group 9D at tip |
| Petalage | 20–25 petals | 60–75 petals |

Parents:

*Seed parent.*—'KORfalt'.

*Pollen parent.*—An unnamed seedling.

FLOWER AND FLOWER BUD

Blooming habit: Continuous.

Flower bud:

*Size.*—Upon opening, 30 mm in length from base of receptacle to end of bud.

*Bud form.*—Long, pointed ovoid.

*Bud color.*—As sepals unfold, Yellow-Orange Group 17B–D. Yellow-Orange Group 16A–B at ¼ opening.

*Sepals.*—Green Group 144B. Strong foliaceous appendages on three of the five sepals. Surfaces of sepals moderately pubescent. Stipitate glands are present on outer surface and edges of sepals.

*Receptacle.*—Surface: Slightly pubescent. Shape: Funnel. Size: Medium. 7 mm (h)×8 mm (w). Color: Yellow-Green Group 144B with anthocyanin noted of Greyed-Purple Group 183B.

*Peduncle.*—Surface: Medium number of stipitate glands. Length: 50–70 mm average length. Color: Yellow-Green Group 144B–C with anthocyanin noted of Greyed-Purple Group 183B. Strength: Upright.

*Borne.*—Singularly.

Flower bloom:

*Fragrance.*—Light and fresh.

*Duration.*—The blooms have a duration on the plant of approximately 10 to 13 days.

*Size.*—Medium. Average flower diameter is 65–70 mm when open.

*Form.*—Shape of flower when viewed from the side: Upon opening, upper part: Cupped. Upon opening, lower part: Flattened convex. Open flower, upper part: Convex. Open flower, lower part: Flattened convex.

Petalage: Double. Average range: 20–25 petals under normal conditions with 2–3 petaloids.

Color:

Upon opening, petals:

*Outermost petals.*—Outer side: Yellow Group 9C. Inner Side: Base: Yellow Group 9C. Marginal zone: Yellow-Orange Group 16B.

*Innermost petals.*—Outer side: Yellow Group 9A. Inner Side: Yellow-Orange Group 16B at margins with an overlap of Red Group 38A–B.

After opening, petals:

*Outermost petals.*—Outer side: Base: Yellow Group 9B. Marginal zone: Yellow Group 5C. Inner Side: Yellow Group 6C–D.

*Innermost petals.*—Outer side: Yellow Group 7AB. Inner Side: Base: Yellow Group 7C. Marginal/Middle Zone: Yellow-Orange Group 19B–C.

General tonality: On open flower Orange Group 21A to Yellow Group 9B. No change in the general tonality at the end of the 6th day. Afterwards, general tonality is Yellow Group 8B.

Petals:

*Petal reflex.*—Slightly.

*Petal edge.*—With point in center of margin.

*Shape: Round.*

*Petaloids.*—Present. Quantity: 3–5.

*Thickness.*—Thick.

*Arrangement.*—Imbricated.

Reproductive organs:

*Pollen.*—Color: Greyed-Orange Group 163A. Quantity: Average.

*Anthers.*—Size: Medium. Color: Greyed Group 160A. Quantity: Average.

*Filaments.*—Color: Yellow Group 13A.

*Stigmas.*—Superior in location to anthers. Color: Greyed-Yellow Group 160A.

*Styles.*—Color: White Group 155A with intonations of Greyed-Yellow Group 160A.

*Hips.*—

PLANT

Plant growth: Vigorous and bushy. When grown as a budded field grown plant on *Rosa multiflora* understock, the average height of the plant is 60–80 cm and the average width is 60–80 cm.

Stems:

*Color.*—Young wood: Yellow-Green Group 144B. Older wood: Yellow-Green Group 144B.

*Thorns.*—Incidence: Moderate. Size: Average length: 4 mm. Color: Greyed-Orange Group 164A to 165A. Shape: Concave.

*Surface.*—Young wood: Smooth. Older wood: Smooth.

Plant foliage: Normal number of leaflets on normal leaves in middle of the stem: 5 leaflets.

*Leaf size.*—Medium. 39 mm (l)×30 mm (w).

*Abundance.*—Very.

*Color.*—Mature Foliage: Upper Leaf Surface: Green Group 137C. Lower Leaf Surface: Green Group 139D. Juvenile foliage: Upper Leaf Surface: Yellow-Green Group 144B. Lower Leaf Surface: Yellow-Green Group 144B. Anthocyanin intonation: Location: Leaf edges. Color: Red-Purple Group 60C.

Plants leaves and leaflets:

*Stipules.*—Size: Medium. 8 mm. Color: Yellow-Green Group 145C–D with Yellow-Green Group 145B at tips of stipules. Stipitate glands present along the leaf margin.

*Anthocyanin.*—Greyed-Purple Group 183B.

*Petiole.*—Length: 9–10 mm. Color: Yellow-Green Group 145B–D with intonations of Yellow-Green Group 144A. Underneath: Yellow-Green Group 145A–B. stipitate glands observed. Margins:

Yellow-Green Group 144A. Anthocyanin: Greyed-Purple Group 183B.

*Rachis.*—Color: Yellow-Green Group 145B–D with intonations of Yellow-Green Group 144A. Underneath: Yellow-Green Group 145A–B. stipitate glands observed. Margins: Yellow-Green Group 144A.

*Leaflet.*—Edge: Serrated. Shape: Broadly ovate. Other: Glossy, thick and leathery.

Disease resistance: Above average resistance to powdery and downy mildew, rust, black spot, and Botrytis under normal growing conditions in Jackson County, Oreg.

Cold hardiness: The variety 'POULdom' has been found to be cold hardy in Fredensborg, Denmark and Jackson County, Oreg.

It is claimed:

1. A new and distinct variety of rose plant of the Floribunda rose class, substantially as herein illustrated and described as a distinct and novel rose variety due to its abundant golden-yellow flowers, disease resistance, and extended period of bloom.

* * * * *

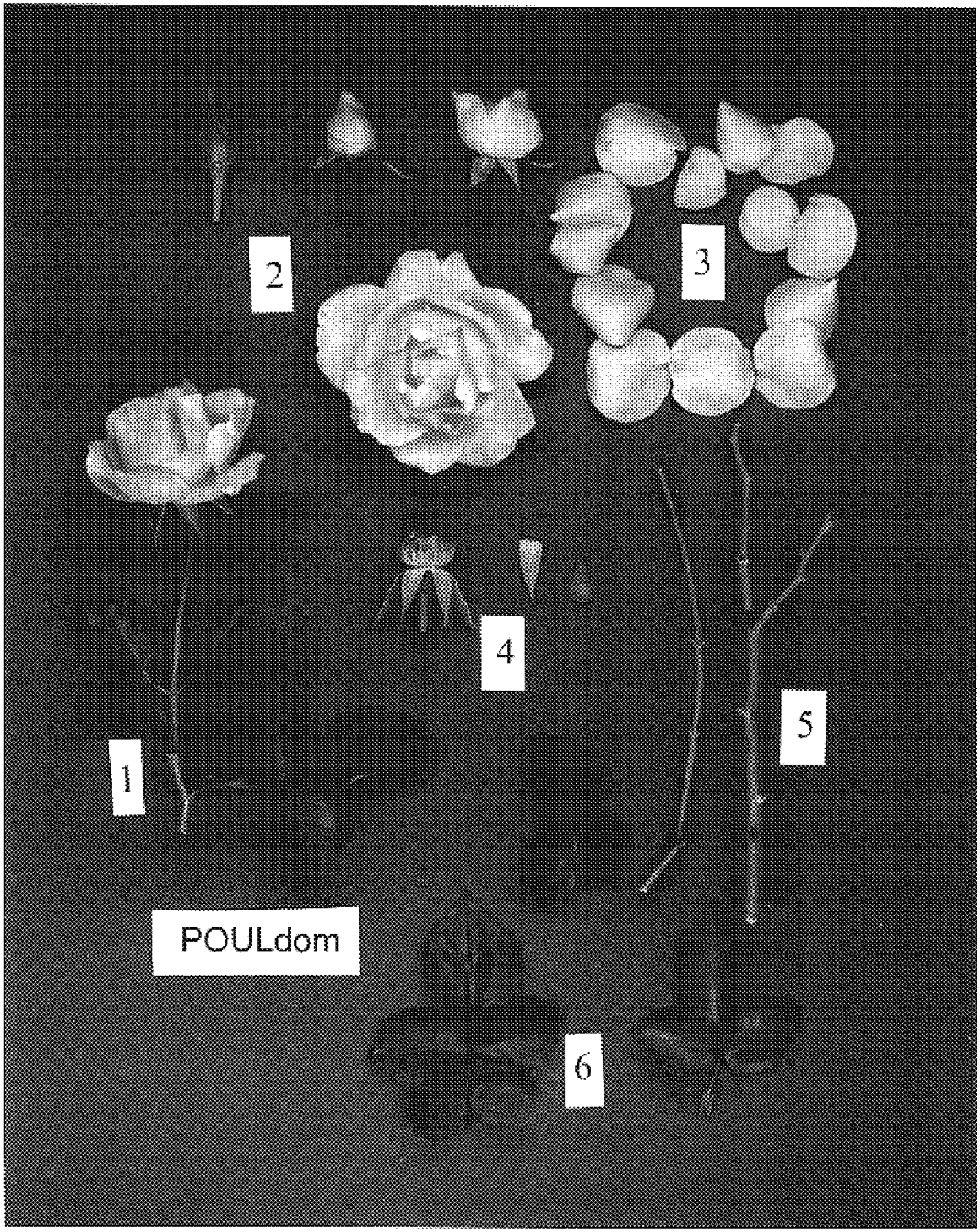
2
3
4
5
1
POULdom
6